United States Patent
Cohen et al.

[19]

[11] Patent Number: 6,065,617
[45] Date of Patent: May 23, 2000

[54] SAMPLE TUBE RACK

[75] Inventors: Beri Cohen, Hartsdale; Thomas DeYoung, Stormville, both of N.Y.

[73] Assignee: Bayer Corporation, Tarrytown, N.Y.

[21] Appl. No.: 09/097,790

[22] Filed: Jun. 15, 1998

[51] Int. Cl.[7] .................................................. A47B 73/00
[52] U.S. Cl. ............................................................ 211/74
[58] Field of Search ................................ 211/74, 71.01, 211/60.1; 206/443; 422/101, 104

[56] References Cited

U.S. PATENT DOCUMENTS

| | | | |
|---|---|---|---|
| 2,467,873 | 4/1949 | Weir | 211/74 |
| 3,109,084 | 10/1963 | Walsh | 211/74 X |
| 3,186,556 | 6/1965 | Frosstrom | 211/74 |
| 3,905,482 | 9/1975 | Knulst | 211/74 |
| 4,534,465 | 8/1985 | Rothermal et al. | 206/443 |
| 5,127,541 | 7/1992 | Wakatake | 206/443 X |
| 5,378,433 | 1/1995 | Duckett et al. | 211/60.1 X |
| 5,427,743 | 6/1995 | Markin | 211/74 X |
| 5,589,137 | 12/1996 | Markin et al. | 211/74 X |

*Primary Examiner*—Alvin Chin-Shue
*Assistant Examiner*—Sarah Purol
*Attorney, Agent, or Firm*—Andrew L. Klawitter, Esq.; Rodman & Rodman

[57] ABSTRACT

The sample rack for holding sample tubes includes a front shell and a rear shell co-joined together in clam shell arrangement. The rack includes tube receiving chambers, each of which has a tube engagement cradle that is arranged to engage a surface portion of a sample tube inserted in the tube receiving chamber. Portions of the tube engagement cradle are formed on each of the front and rear shells and the co-joining of the shells completes the structure of the tube engagement cradle. Each tube receiving chamber also includes a depending biasing spring leg that urges the sample tube toward the tube engagement cradle. The rack also includes spring mount portions for supporting biasing springs that incorporate the biasing spring legs. Segments of the spring mount portion are also formed on each of the front and rear shells and the co-joining of the shells completes the structure of the spring mount portion.

20 Claims, 8 Drawing Sheets

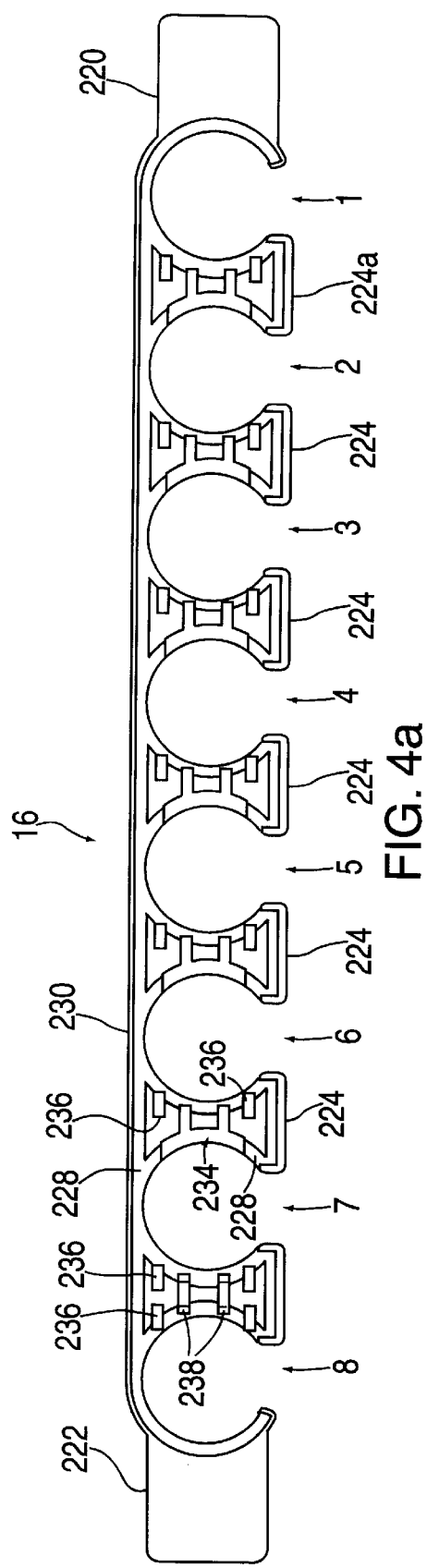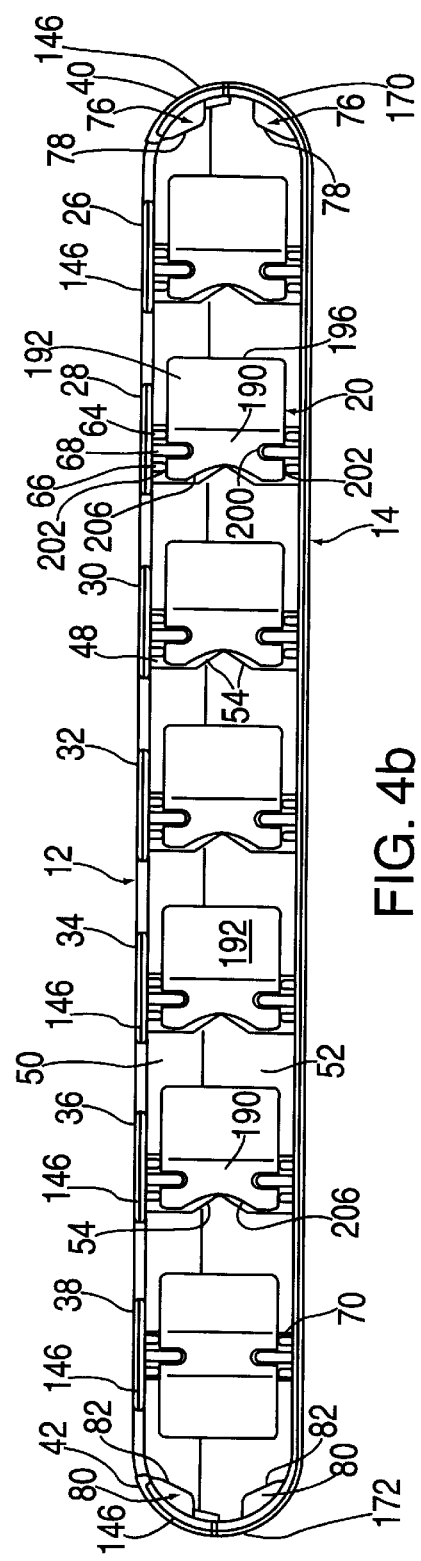

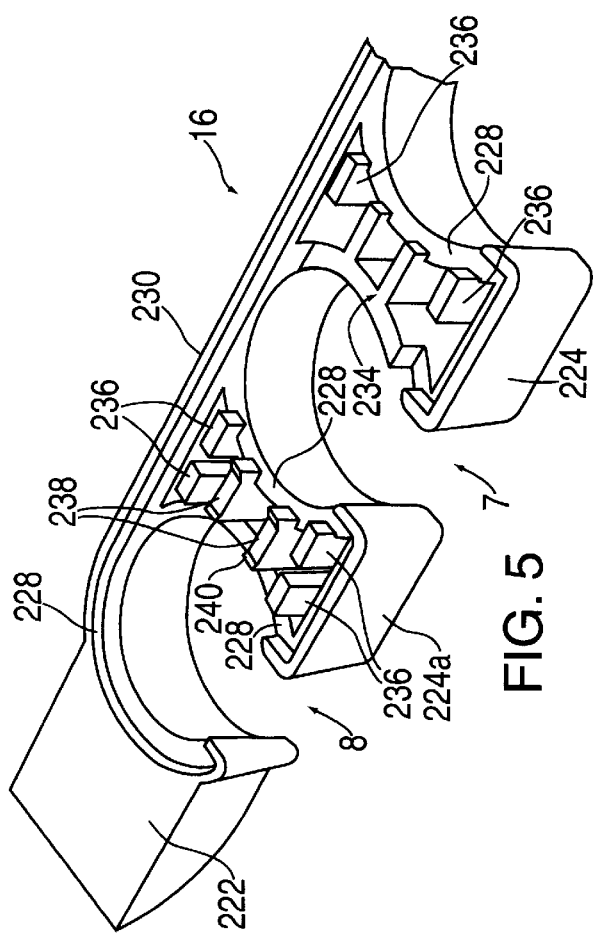
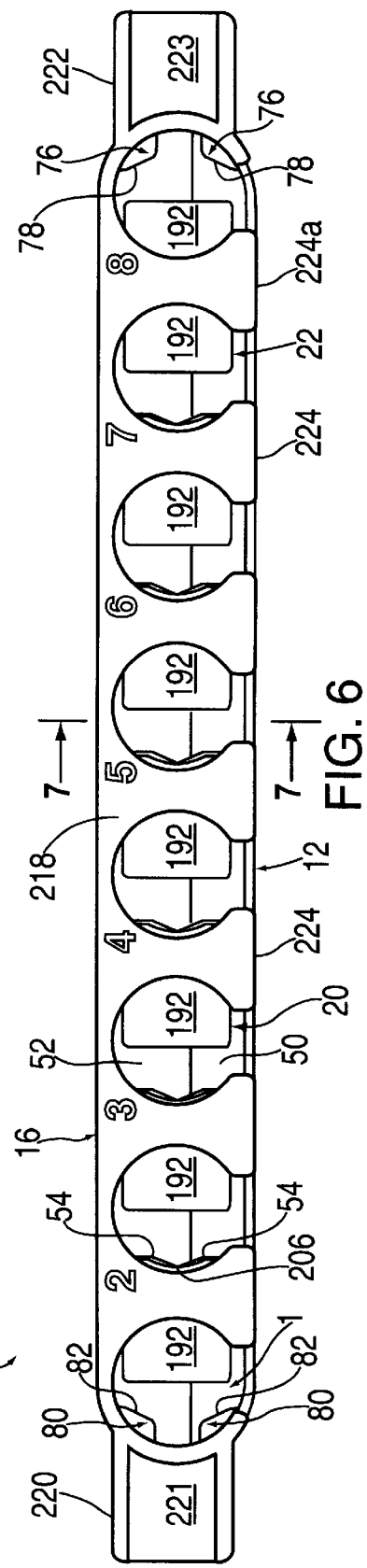
FIG. 5
FIG. 6

SAMPLE TUBE RACK

BACKGROUND OF THE INVENTION

This invention relates to racks for holding sample tubes, and more particularly to a sample tube rack for automatic transport of a plurality of sample tubes to be unloaded at the receiving area of a sample analysis system, and later reloaded at an exit area of the sample analysis system for removal.

High volume testing of body fluids, such as blood samples, is usually carried out in an automatic sampling system for sample analysis. The automatic sampling system, which operates with a minimum of human intervention, automatically withdraws samples from a sample tube in selected amounts for automatic testing and analysis. The test apparatus in known automatic sampling systems are generally adapted to perform one or more specific tests or a battery of tests on discrete amounts of sample that are withdrawn from a sample tube.

In some instances it is desirable to transport the sample tubes to the receiving area of the sample analysis system in one type of sample tube rack, and then transport the sample tubes within the automatic analysis system in another type of sample tube rack. Whenever a sample tube is transferred from one sample tube rack to another sample tube rack there must be stability of the rack during the transfer process. It is also important that the sample tubes in the rack be held with sufficient retention force to maintain stability of the tubes in the rack during their journey from one point to another. However, any retention force applied to the sample tubes in the rack should also permit easy release for unloading of tubes from the rack and easy installation of the sample tubes into the rack when it is reloaded after testing of the samples in the sample tubes is completed.

It is also beneficial that the rack be able to accommodate sample tubes of different length and diameter without adversely affecting the loading and unloading facility of the rack.

It is thus desirable to provide a sample tube rack that can be easily constructed and assembled for automatic transport at relatively high speeds while maintaining stable accommodation of the sample tubes in the rack during such transport.

OBJECTS AND SUMMARY OF THE INVENTION

Accordingly, it is an object of the invention to provide a novel sample tube rack which can accommodate sample tubes of different length and diameter without adversely affecting the loading and unloading facility of the rack. It is a further object of the invention to provide a novel sample tube rack which will be stable whenever a sample tube is transferred in or out of the sample tube rack. It is yet a further object of the invention to provide a novel sample tube rack having one biasing spring structure for each tube chamber of one group of tube chambers in the rack and another biasing spring structure for a second group of tube chambers in the rack to exert a retention force that maintains stability of the tubes in the rack and permits easy loading and unloading of tubes. It is still a further object of the invention to provide a novel sample tube rack which utilizes a simple, clamshell mating assembly. Another object is to provide features on the rack that permit reading of bar code labels on sample tubes installed in the rack. Still another object is to provide features on the rack that facilitate grouped lifting of a plurality of racks. Another object is to provide features on the rack that permit automatic movement of the rack in three dimensions. A still further object of the invention is to provide the rack with surface characteristics that facilitate liquid level sensing of samples in the rack. An additional object of the invention is to provide a sample tube rack that can be automatically transported at relatively high speeds without loss of stability.

Other objects and features of the invention will be in part apparent and in part pointed out hereinafter.

In accordance with the present invention, the sample tube rack includes a front shell and a rear shell joined together in clam shell arrangement. Each shell includes floor sections, partition sections and latch portions that align when the shells are mated. The shells also include support for a ballast member that enhances the stability of the rack. Biasing springs are supported atop the aligned partition sections and depend into tube receiving chambers defined by the assembled front and rear shells. A top portion of the rack is fitted onto the assembled shells after the biasing springs are positioned on the aligned partition sections. Open spaces or window openings are provided in the front shell of the rack to permit reading of bar code labels on sample tubes installed in the rack.

The rack also includes base recesses engageable by a transport device and a window opening in a wall of each base recess that are engageable by a hold down device to facilitate loading and unloading of tubes from the rack and lateral movement of the rack. Tabs formed at the ends of the rack permit vertical movement of the rack, and the two base recesses at the bottom of the rack are engageable by tracks that have a rectilinear movement to provide forward and rearward movement of the rack. The engagement of racks in the base recesses also prevent skewing of the rack during such forward and rearward movement. Ribs formed on the front and rear shells of the rack mesh with corresponding ribs on other racks to permit grouped lifting of a plurality of racks.

The invention accordingly comprises the constructions hereinafter described, the scope of the invention being indicated in the claims.

DESCRIPTION OF THE DRAWINGS

In the accompanying drawings,

FIG. 4a is a bottom plan view of the top cover of the rack;

FIG. 4b is a top plan view of the rack without the top cover;

FIG. 5 is an enlarged fragmentary perspective view of the left end portion of the top cover as shown in FIG. 4a;

FIG. 6 is a top plan view of the rack with the top cover;

Corresponding reference characters indicate corresponding parts throughout the several views of the drawings.

DETAILED DESCRIPTION OF THE INVENTION

Figure 1:
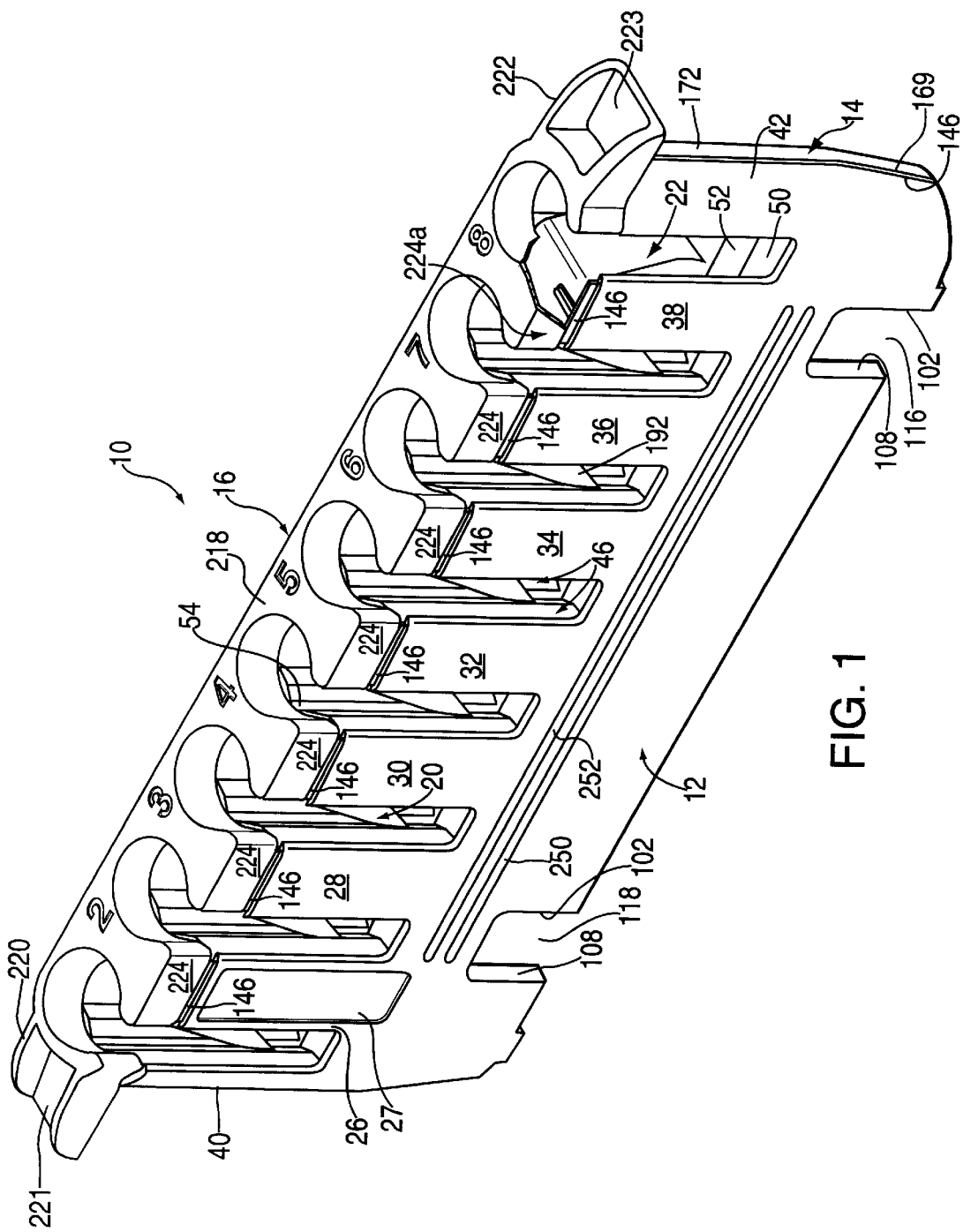
FIG. 1 is a top perspective view of a sample tube rack incorporating one embodiment of the invention.

Referring to the drawings, a sample rack incorporating one embodiment of the invention is generally indicated by the reference number 10. As most clearly shown in FIG. 3 the rack 10 includes a front shell 12, a rear shell 14, and a top cover 16. The rack also includes a plurality of single legged leaf springs 20 and a double legged leaf spring 22.

Figure 3:
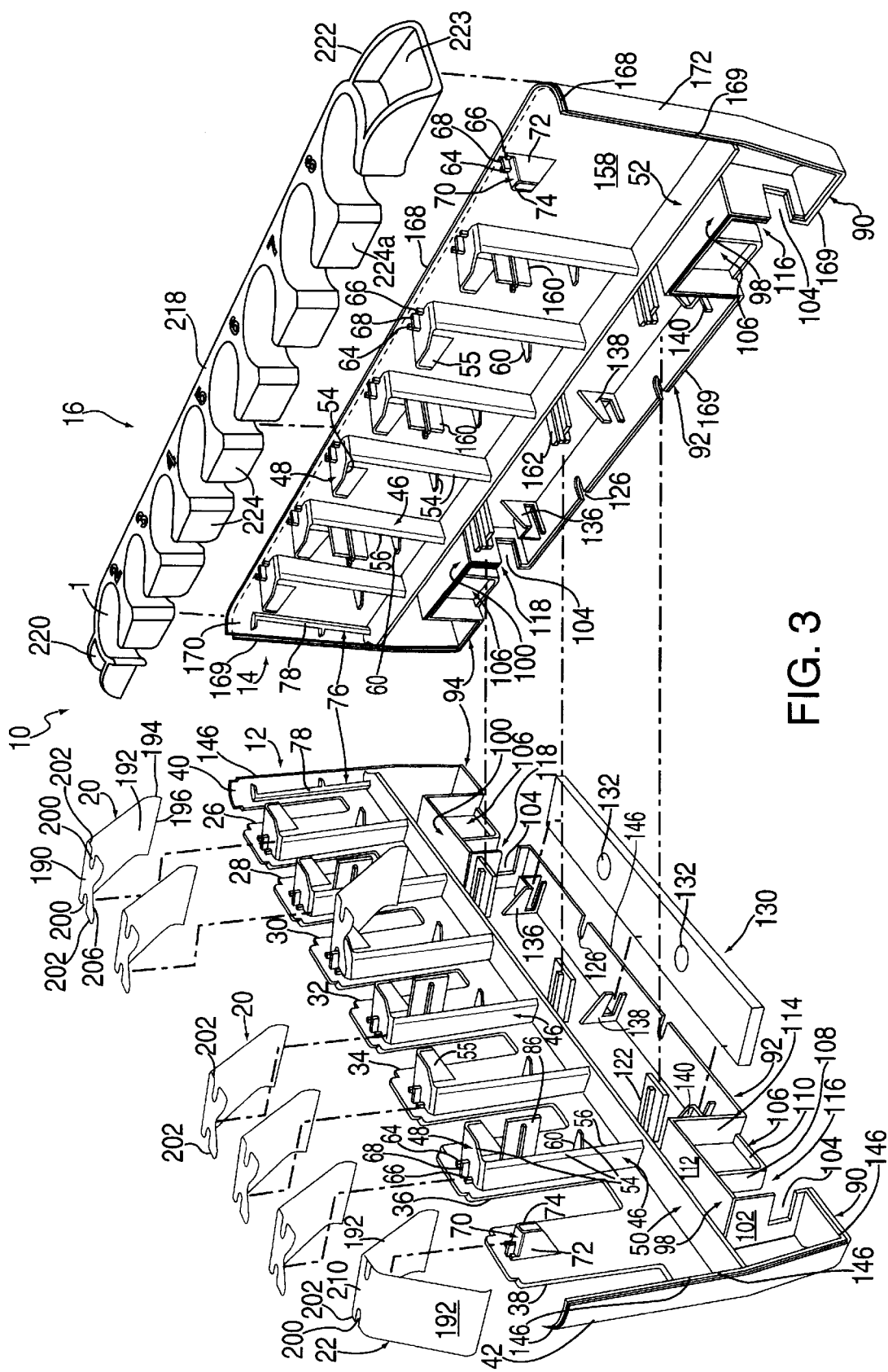
FIG. 3 is an exploded view thereof.
Figure 9:
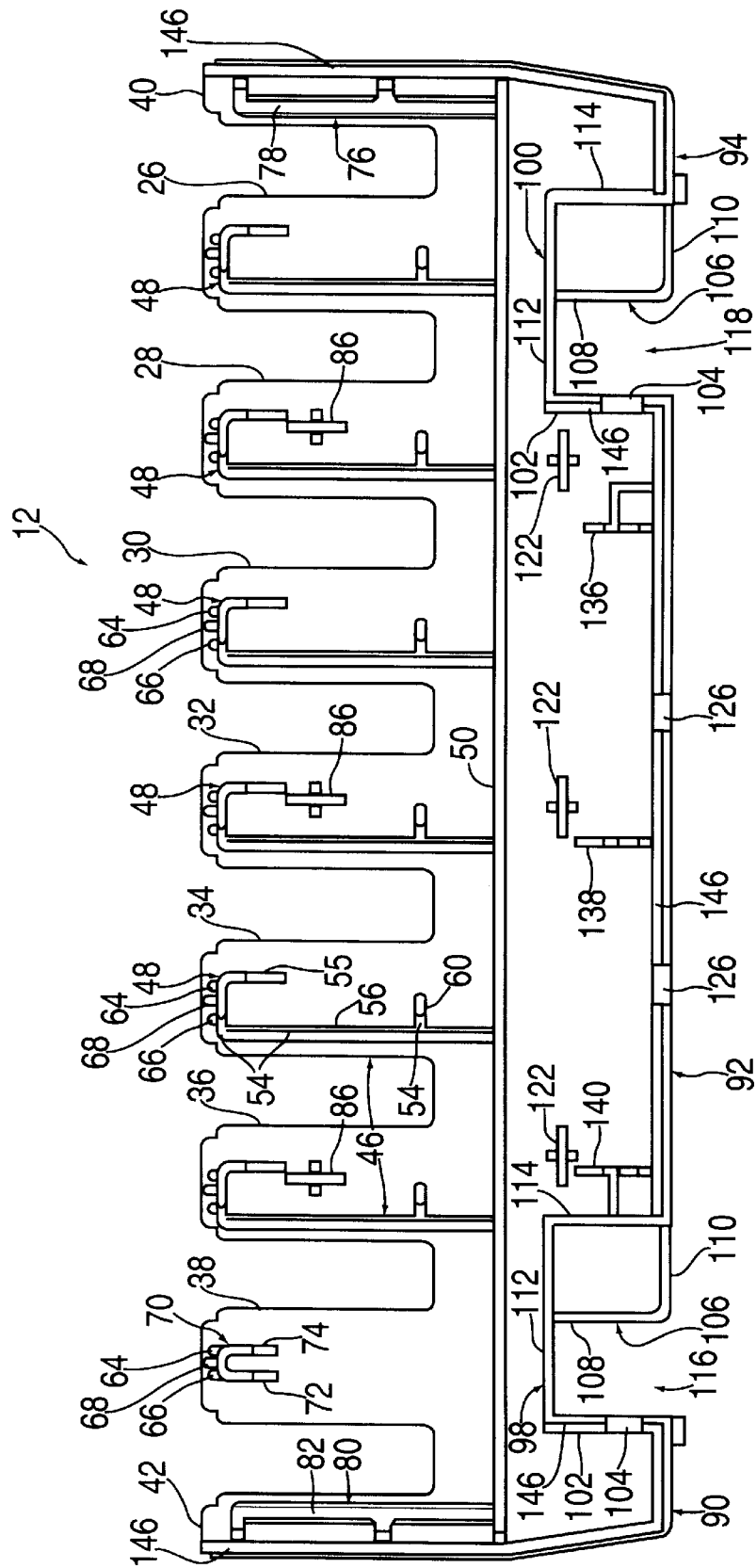
FIG. 9 is a plan view of the left shell portion of the rack as shown in FIG. 3.

Referring to FIGS. 3 and 9, the front shell 12 includes spaced wall portions 26, 28, 30, 32, 34, 36, 38, and opposite curved end portions 40 and 42. The spaces between consecutive wall portions 26–38 and the spaces between the curved end portions 40, 42 and the adjacent wall portions 26 and 38 permit reading of a bar code label (not shown) on sample tubes that are installed in the rack 10. The wall portion 26 has a recessed area 27 (FIG. 1) for provision of a bar code label. The wall portions 26–36 are formed with identical partition sections 46 which each include a spring mount portion 48 at an upper end, the opposite lower end joining a platform section 50 that extends to the curved end portions 40 and 42. Each spring mount portion 48 has a beveled tube engagement surface 54 and an opposite downwardly extending gusset 55. The beveled tube engagement surface 54 is also provided at a free edge 56 of the partition section 46 and at a gusset 60 that reinforces the partition section 46. Two short spring positioning protrusions 64 and 66 are formed on the spring mount portion 48 with a longer spring positioning protrusion 68 located between the protrusions 64 and 66.

The shell 12 further includes a spring mount portion 70 (FIG. 3) at the wall portion 38. The spring mount portion 70 includes opposite depending side gussets 72 and 74 and the short protrusions 64, 66 and the long protrusion 68 (FIG. 9).

A tube engagement riser 76 is formed at the curved end portion 40 and has a beveled vertical surface 78 (FIG. 4b) having the same bevel angle as the bevel 54 although oppositely inclined. A symmetrical tube engagement riser 80 (FIG. 4b) is formed at the curved end portion 42 and has a beveled vertical surface 82 having the same bevel angle as the beveled surface 78.

Identical male latch components 86 project from each of the wall portions 28, 32 and 36.

Referring to FIGS. 3 and 9 a lower portion of the front shell 12 below the platform section 50 includes base sections 90, 92 and 94. A three-sided U-shaped formation 98 connects the base section 90 to the base section 92. A three-sided U-shaped formation 100 similar to the U-shaped formation 98 connects the base section 92 to the base section 94. A side 102 of the U-shaped formation 98 is formed with a window cutout 104. A corner section 106 with sides 108 and 110 is joined to side portions 112 and 114 of the U-shaped formation 98. A track recess 116 (FIG. 1) is thus defined proximate the curved end portion 42 of the front shell 12 between the side 108 (FIG. 9) of the corner section 106 and the side 102 of the U-shaped formation 98. A track recess 118 similar to the track recess 116 is defined proximate the curved end portion 40 of the front shell 12 between the side 108 of the corner section 106 and the side 102 of the U-shaped formation 100.

Three male latch components 122, similar to the male latch components 86 are provided between the platform section 50 and the base section 92 but are oriented 90 degrees out of phase with the latch components 86. The base section 92 includes drainage openings 126.

A metal ballast member 130 (FIG. 3) having drainage openings 132 is supported in ballast holders 136, 138 and 140 that are gusset-like formations at the base portion 92 of the shell 12. Suitable known crush ribs (not shown) can be provided at the holders 136 and 140 to securely retain the ballast member 130 in the ballast holders 136 and 140.

A step 146 (FIG. 3) is provided at the top edge of the curved end portion 42 and extends downwardly along the curved portion 42, along the free edges of the base sections 90, 92 and 94 and along the free edges of the wall sections 102 of the U-shaped formations 98 and 100. The step 146 is also provided at the top of each wall portion 26–38 as most clearly shown at the wall portion 38 in FIG. 1.

Figure 10:
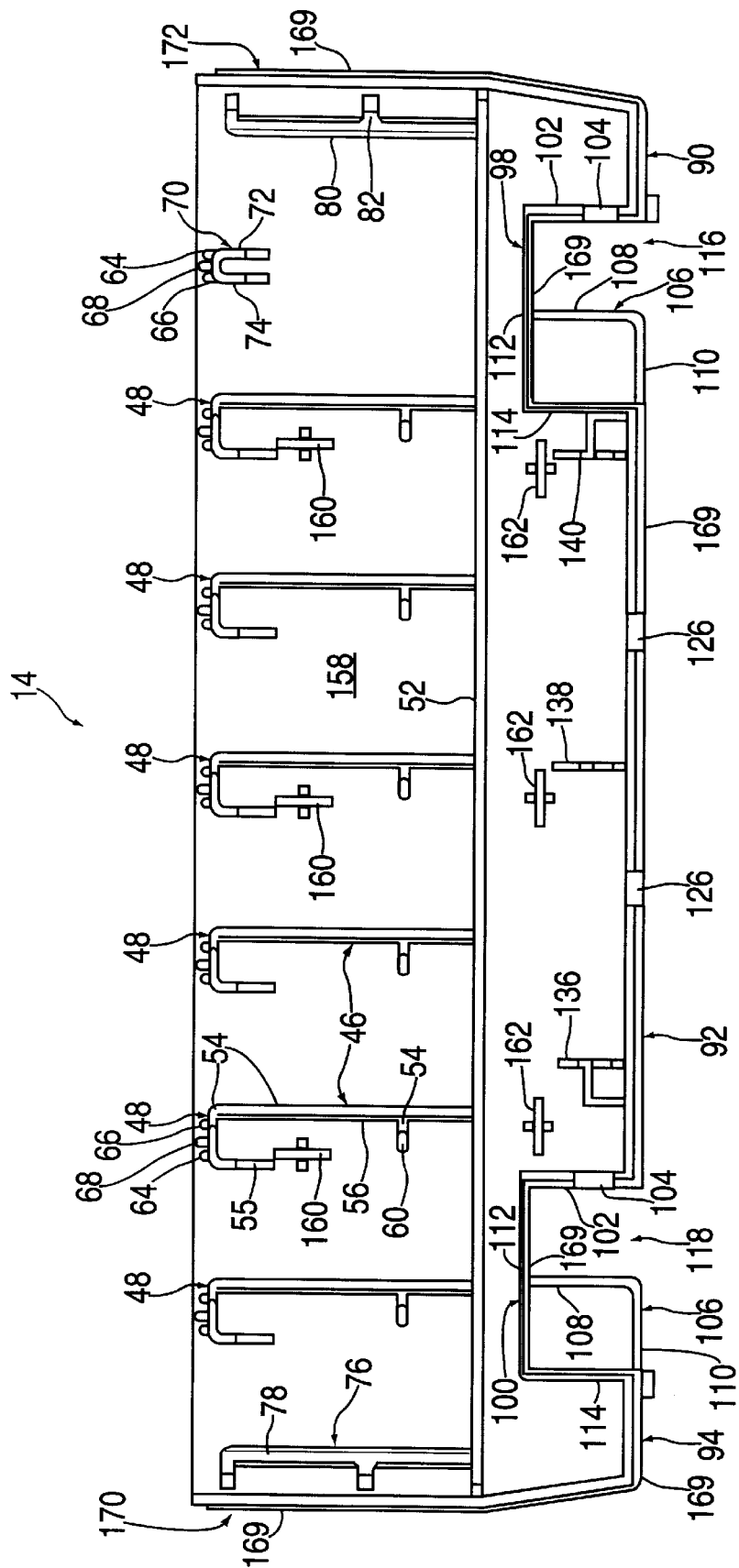
FIG. 10 is a plan view of the right shell portion of the rack as shown in FIG. 3.

Referring to FIGS. 3 and 10 the rear shell 14 includes a vertical wall portion 158 with three female latch components 160 positioned opposite the male latch components 86 of the shell 12 and three female latch components 162 positioned opposite the male latch components 122 of the shell 12.

A top edge of the wall portion 158 is formed with a step 168 that is similar to the step 146 of the front shell 12. A step 169 that is complementary with the step 146 of the shell 12 extends downwardly along curved end portions 170 and 172 of the rear shell 14. The step 169 is formed at the base portions 90, 92 and 94 of the rear shell 14 and at the free edges of the U-shaped formations 98 and 100. The rear shell 14 also includes some structural features that are symmetrical to the structural features already described for the front shell 12 and such symmetrical features are indicated by corresponding reference numbers.

Figure 2:
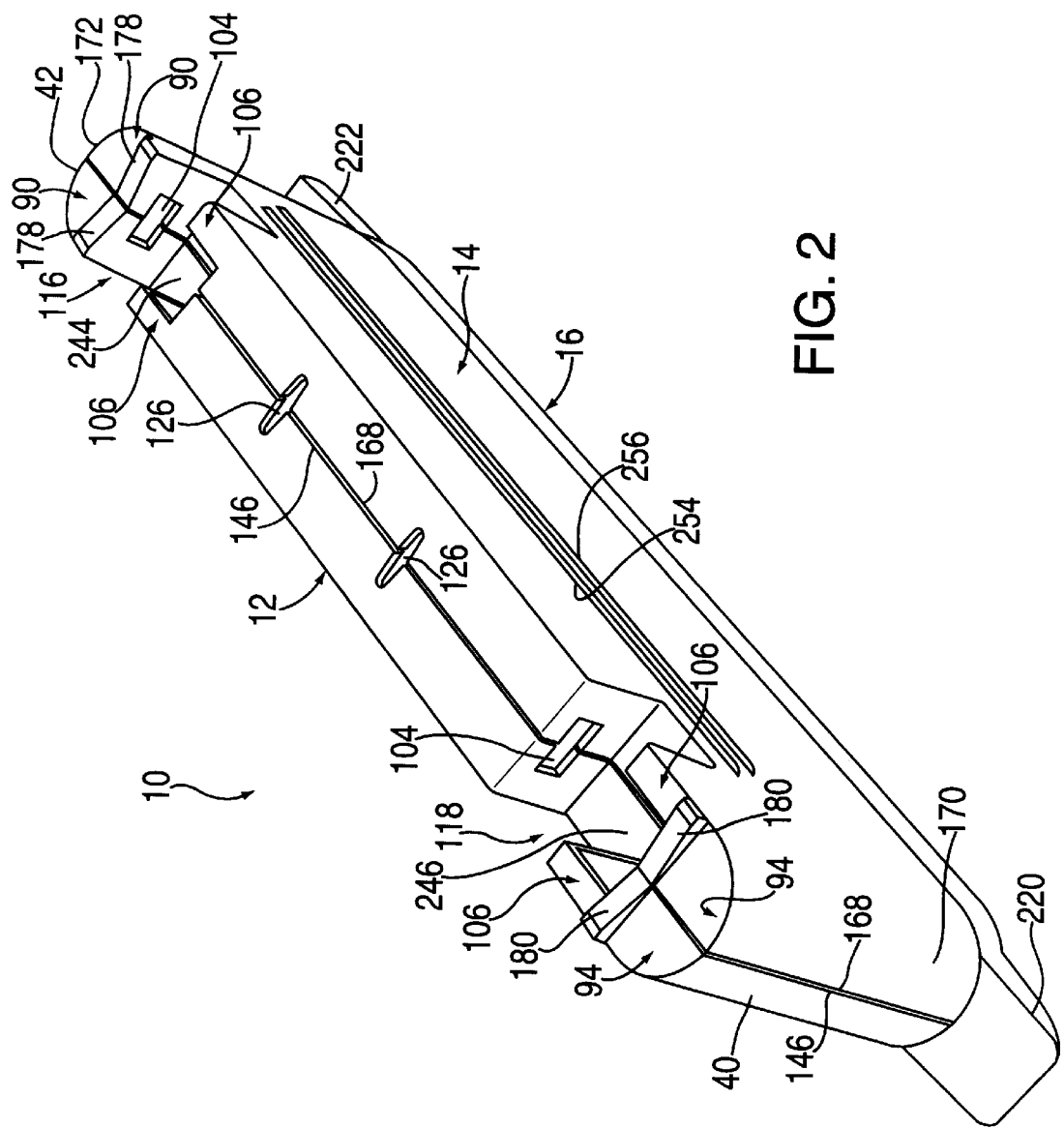
FIG. 2 is a bottom perspective view thereof.

As most clearly shown in FIGS. 2, 9 and 10, foot sections 178 and 180 are provided at the respective base sections 90 and 94.

Referring to FIG. 3 the springs 20 include a mounting section 190 and a biasing leg 192 extending downwardly from the mounting section 190 at an angle of approximately 30° to the vertical. An inward bend 194 (FIG. 3) is provided at a free end 196 of the biasing leg 192. The spring mounting section 190 includes opposite grooves 200 for engagement with the long protrusions 68 of the spring mount 48, and opposite side edges 202 for abutment against the free ends of the short protrusions 64 and 66. The mounting section 190 is also formed with a concave recess 206.

The double legged spring 22 includes two diverging biasing legs 192 that depend from a mounting portion 210. The mounting portion 210 also includes the oppositely disposed grooves 200 in the side edges 202. Preferably the springs 20 and 22 are formed of stainless steel such as spring type 302 having a thickness of approximately 0.15 mm.

Referring to FIG. 3 the top cover 16 of the rack 10 is formed with eight chamber openings, seven of which are indicated by the numbers 2,3,4,5,6,7 and 8 molded on a surface 218 to the left of the corresponding chamber opening. The first chamber opening is indicated by the reference number 1. The top cover 16 also includes opposite end tabs 220 and 222 that have sufficient length to permit finger lifting of the rack 10 at the tabs. The tabs 220 and 222 can also be engaged by a walking beam (not shown) that may be used for movement of the rack 10. The tabs 220 and 222 also include respective labeling surfaces 221 and 223 for provision of a suitable known labeling device (not shown).

The top cover 16 also includes six front flange sections 224 between adjacent chambers in the group of chambers 1 through 7. A front flange section 224a is provided between the adjacent chambers 7 and 8. The flange sections 224 and 224a form continuations of the wall portions 26–38 of the shell 12 when the top cover 16 is assembled to the front and rear shells 12 and 14 of the rack 10.

Referring to FIG. 4a, the front flange sections 224 and 224a are stepped away from a recessed surface 228. A rear wall 230 of the top cover 16 is also stepped away from the surface 228 to substantially the same extent as the front flange sections 224 and 224a. A pi ($\pi$)-shaped projection 234 and two narrow dash (–) shaped projections 236 are provided between each flange 224 and the rear wall 230. The projections 236 and 238 are stepped away from the surface 228 to a slightly greater extent than the front flange section 224 and the rear wall 230.

Referring to FIGS. 4a and 5, two pairs of the narrow dash (–) shaped projections 236 are provided opposite a pair of wide dash (-) shaped projections 238 between the flange portion 224a and the rear wall 230 of the top portion 16. The projection 238 projects from the surface 228 to the same extent as the projection 236. The wide projections 238 include projecting beveled end portions 240 (FIG. 5).

The rack 10 is assembled by placing the ballast member 128 in the ballast holding portions 136, 138 and 140 of one the shells 12, 14. Both of the shells 12 and 14 are joined together so that the ballast holding portions 136, 138 and 140 of each shell align and enable the male and female latch components 86, 122, 160 and 162 of each shell to engage. The partition sections 46 of each of the shells 12 and 14 are aligned such that the spring mount portions 48 and the gussets 60 abut. The beveled surface portions 54 of the free edges 56 of the partition sections 46 are spaced from each other as most clearly shown in FIG. 1. The beveled surface portions 54 of the aligned partition sections 46 of each shell 12, 14 form V-shaped tube engaging cradles as most clearly shown in FIGS. 1 and 4b. The abutting spring mount portions 48 of each shell 12, 14 form a horizontal support for the mounting sections 190 of each of the springs 20.

The springs 20 are positioned on the spring mount portions 48 by aligning the grooves 200 of the spring mounting section 190 with the long protrusion 68 on the spring mount portion 48. The opposite side edges 202 of the spring mounting sections 190 thus abut against the ends of the short protrusions 64 and 66. With the springs 20 thus supported on the spring mount portions 48 the spring biasing leg 192 extends downwardly in each of the chambers 1–6. The spring mount portions 70 likewise abut to form a horizontal mounting surface for the mounting section 210 of the spring 22. With the spring 22 supported on the mounting portion 70 the diverging spring biasing legs 192, 192 extend downwardly at opposite angles in the chambers 7 and 8.

When the front and rear shells 12, 14 are engaged as described, the step portion 146 of the shell 12 engages the complementary step portion 169 of the shell 14 wherever the shells 12, 14 make edge to edge contact.

It will be noted that the platform section 50 of the front shell 12 is narrower than the platform section 52 of the rear shell 14 as most clearly shown in FIGS. 4b, 6, 7 and 8. The difference in platform section width insures that the bottom of the sample tubes 92 in the rack 10 sit on the wider platform section 52 rather than on a clam shell dividing line if the platform sections 50 and 52 were of equal width.

The top cover 16 is placed on the assembled front and rear shells 12,14 and over the mounted springs 20 and 22. The stepped edges of the top cover flanges 224 and 224a and the stepped edge 230 of the top cover wall 230 engage the complementary stepped portions 146 and 168 at the top edges of the front and rear shells 12, 14. The projection 234, 236 and 238 between the flanges 224, 224a and the rear wall 230 of the top cover 16 press against the mounting sections 190 and 210 of the springs 20 and 22, to sandwich the mounting sections 190 and 210 in a fixed position between the top cover 16 and the respective spring mounts 48 and 70.

Preferably the shells 12 and 14 and the top cover 16 are ultrasonically bonded in any suitable known manner to form a permanent securement.

Referring to FIGS. 1 and 2 the recesses 116 and 118 of the assembled rack 10 are engageable by a track (not shown) for transport of the rack and to prevent skewing of the rack. The recesses 116 and 118 also communicate with respective clearance spaces 244 and 246 between the spaced and confronting corner sections 106.

Referring to FIG. 1 the front shell 12 includes two elongated spaced ribs 250 and 252 and the rear shell includes a pair of similar sized spaced ribs 254 and 256. The ribs 250, 252 are slightly offset from the ribs 254, 256 as most clearly shown in FIGS. 7 and 8. Under this arrangement when a plurality of the racks 10 are placed in adjacent front shell to rear shell contact the ribs 250, 252 of one rack 10 interengage with the ribs 254, 256 of another rack 10 to permit grouped lifting of a plurality of the racks 10.

Figure 7:
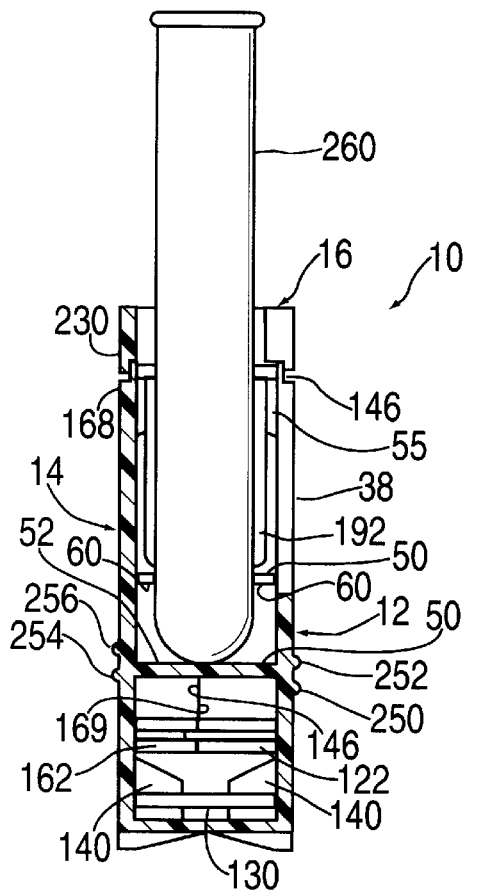
FIG. 7 is a sectional view taken on the line 7—7 of FIG. 6 and including a test tube installed therein.
Figure 8:
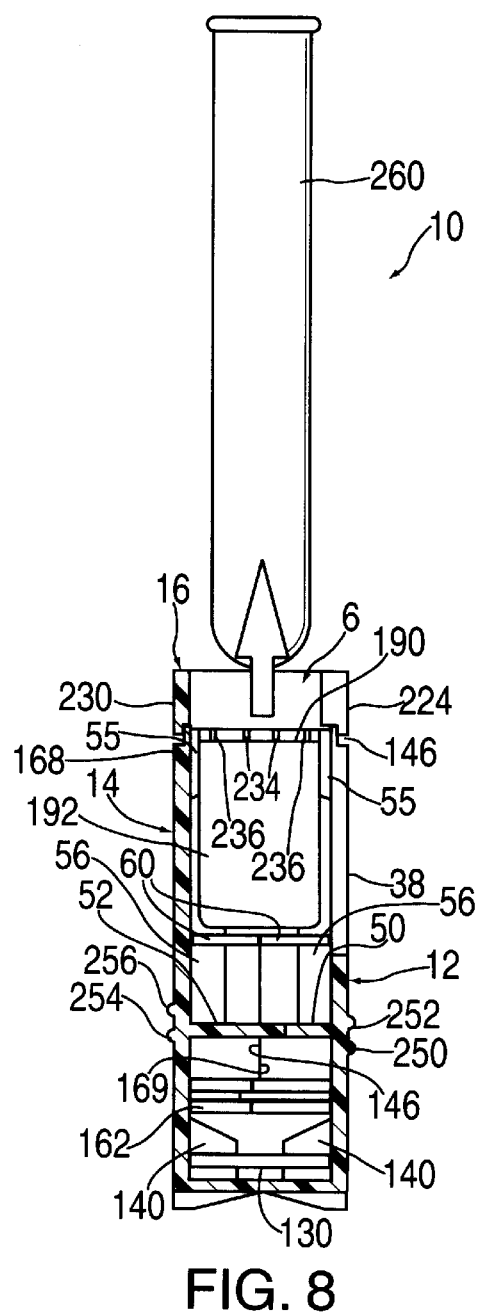
FIG. 8 is a sectional view similar to FIG. 7 with the test tube withdrawn from the rack.

Referring to FIGS. 7 and 8 insertion of a sample tube 260 into any of the chambers 2–7 enables the biasing leg 192 of the spring 20 to bias the sample tube 260 against aligned beveled surfaces 54 of each shell 12, 14 that define the V-shaped tube engagement cradle portion of the respective chambers. The chambers 1 and 8 are provided with beveled tube engaging surfaces 78 and 82 on the symmetrical riser portions 76 and 78 at the curved end portions 40, 42 and 170, 172 of the respective shells 12, 14. The aligned beveled tube engagement surfaces 78, 78 and 82, 82 of each shell 12, 14 define a V-shaped tube engagement cradle for the chambers 1 and 8.

The biasing legs 192 and the tube chambers 1–8 can accommodate different sample tube diameters such as 12 mm and 16 mm tubes and ensure that tubes within this size range are adequately spaced in the rack 10 to permit robotic insertion and removal of the tubes from the rack. For example, referring to FIG. 3, the distance between the gusset 55 of one partition section 46 and the apex of the tube engaging cradle of an adjacent partition section 46 can be approximately 19 mm. The distance between the intersection point of the beveled surfaces 78, 78 for example and the gusset 72 is also approximately 19 mm. The distance between the gusset 55 and the apex of a tube engaging cradle of the spring mount portion 48 can be approximately 6 mm. The outside distance between the gussets 72 and 74 of the spring mount portion 70 can be approximately 5 mm.

The windows 104, 104 of the rack 10 are engageable by hold down fingers (not shown) for holding the rack in a stable upright position during insertion and removal of tubes from the rack. The recesses 116, 118 and the clearance spaces 244, 246 (FIG. 2) facilitate entry of the hold down fingers in the windows 104 and permit transverse movement of the hold down fingers toward and away from the windows 104.

The rack is formed of any suitable known plastic and selected horizontal surfaces 50, 52, 218, 221, and 223 or all of the rack surfaces that are visible when the rack is assembled can be finished in a known manner in accordance with the Society of Plastics Industry Specification D-2 for the finishing of plastic surfaces, to provide acoustic reflective surfaces that function as a reference level for liquid level sensing and tube identification.

Some advantages of the present invention evident from the foregoing description include a rack of clam shell construction that can be simply manufactured and assembled. A farther advantage is the incorporation of a relatively simple biasing spring structure that can be easily positioned and held in place in the rack. Another advantage is the provision of readout windows in the rack to permit reading of bar code labels on sample tubes installed in the rack. A further advantage is the provision of hold down windows in the rack which are engageable by a hold down device to permit selective application of a hold down force that facilitates loading and unloading of the rack. Still another advantage of the rack is the provision of ribbed formations on the front and rear shells in staggered arrangement that permit engagement of the ribs of one rack with the ribs of another rack to permit grouped lifting of a plurality of racks. Still other advantages are the provision of features on the rack that permit automatic movement of the rack in three dimensions.

As various changes can be made in the above constructions without departing from the scope of the invention, it is intended that all matter contained in the above description or shown in the accompanying drawings shall be interpreted as illustrative and not in a limiting sense.

What is claimed is:

1. A sample rack for holding sample tubes comprising,
   a) a front shell having a plurality of spaced front shell tube engagement surfaces,
   b) a rear shell formed separately from the front shell and having a corresponding plurality of spaced rear shell tube engagement surfaces,
   c) said front and rear shells being co-joined and a corresponding plurality of tube receiving chambers are defined by said co-joined front and rear shells,
   d) each of said tube receiving chambers having a tube engagement cradle defined by corresponding front and rear shell tube engagement surfaces, said tube engagement cradles being engageable with surface portions of sample tubes inserted into said tube receiving chambers, and,
   e) a biasing spring leg in each of said chambers to provide a biasing force directed toward a corresponding tube engagement cradle to urge sample tubes in said tube receiving chambers against said tube engagement cradles.

2. The sample rack as claimed in claim 1 further including a predetermined number of spring mount portions, each of said spring mount portions supporting a spring member, each of said spring members having at least one of said biasing spring legs.

3. The sample rack as claimed in claim 2, wherein one of said spring members supported by said spring mount portion has two of said biasing spring legs.

4. The sample rack as claimed in claim 3, wherein said two biasing spring legs of said one spring diverge from each other.

5. The sample rack as claimed in claim 2, wherein each of said biasing spring legs are downwardly directed from said spring mounts into said tube receiving chambers.

6. The sample rack as claimed in claim 5, wherein said biasing spring legs have a free end and said biasing spring legs diverge away from said spring mount such that said free end is directed toward a corresponding said tube engagement cradle.

7. The sample rack as claimed in claim 2, wherein at least one of said spring mount portions for one said chamber include said front shell and said rear shell tube engagement surfaces for another said chamber.

8. The sample rack as claimed in claim 2, wherein each of said spring members includes a spring mount section located on respective said spring mount portions.

9. The sample rack as claimed in claim 8, including a top cover for said co-joined front and rear shells arranged to fit onto said front and rear shells such that said spring mount sections are sandwiched between said top cover and said spring mount portions.

10. The sample rack as claimed in claim 8, wherein said spring mount section includes locating grooves and said spring mount portion includes locating projections to fit in said locating grooves to position said spring mount section on said spring mount portion.

11. The sample rack as claimed in claim 1 wherein said rack includes a platform that forms a floor of said tube receiving chambers, said front shell and said rear shell each including a section of said platform, one of said platform sections being of a predetermined greater width from one of said shells to the other said shell than the other said platform section to insure that a sample tube in any of said chambers bottoms against only said one platform section.

12. The sample rack as claimed in claim 1 wherein readout windows are provided in one of said shells in alignment with said tube receiving chambers to permit automatic reading of bar code labels provided on said sample tubes.

13. The sample rack as claimed in claim 1, wherein said front and rear shells include a bottom portion and a pair of spaced recesses are formed in the bottom portion of said front and rear shells whereby an automatic transport device for transport of the rack is positionable in said spaced recesses.

14. The sample rack as claimed in claim 13, wherein each of said recesses is bordered by a vertical wall and an opening is formed in each of said vertical walls whereby a hold down device is positionable in each of said openings to hold down the rack during unloading of sample tubes.

15. The sample rack as claimed in claim 1, including a pair of spaced and parallel horizontal ribs formed on said front and rear shells, the pair of ribs on said front shell being offset from the pair of ribs on said rear shell whereby the ribs on the front shell of said rack can mesh with the ribs on the rear shell of another said rack to permit grouped lifting of said racks.

16. The sample rack as claimed in claim 1 including support means on each of said front and rear shells for holding a ballast member between said cojoined front and rear shells.

17. The sample tube rack as claimed in claim 1 wherein said rack includes a bottom portion with a pair of spaced recesses, said front shell and said rear shell including a portion of said spaced recesses whereby said spaced recesses serve an anti-skewing function during automatic transport of said rack.

18. The sample tube rack as claimed in claim 12 wherein said rack has a top portion and a bottom portion and a plurality of horizontal surfaces that are visible when said rack is viewed in a direction from said top portion to said bottom portion, said horizontal surfaces being formed with a predetermined finish to provide acoustic reflective surfaces that function as a reference for liquid level sensing of sample tube liquid in sample tubes disposed in said rack.

19. A sample rack for holding sample tubes comprising,
   a) separately formed front and rear shells co-joined to form a first predetermined number of tube receiving chambers,
   b) each of said tube receiving chambers having a tube engagement cradle and a biasing spring leg for biasing a sample tube in the tube receiving chamber toward the tube engagement cradle, and
   c) said front and rear shells each being formed with a portion of said tube engagement cradle.

20. The sample rack as claimed in claim 19, wherein at least one of said tube engagement cradles is formed without a spring mount.

* * * * *